US00PP10557P

United States Patent [19]

Flemer, III

[11] Patent Number: Plant 10,557

[45] Date of Patent: Aug. 18, 1998

[54] *MAACKIA AMURENSIS* PLANT NAMED 'STARBURST'

[75] Inventor: William Flemer, III, Plainsboro Township, Middlesex County, N.J.

[73] Assignee: Newplant Associates, Allentown, N.J.

[21] Appl. No.: 754,087

[22] Filed: Nov. 20, 1996

[51] Int. Cl.[6] ..... A01H 5/00

[52] U.S. Cl. ..... Plt./51.1

[58] Field of Search ..... Plt./51.1

[56] References Cited

PUBLICATIONS

Huxley, et al., (Eds.) "Maackia", The New Royal Horticultural Dictionary of Gardening—3, 1992, The Stockton Press, New York, p. 174.

*Primary Examiner*—James R. Feyrer

*Attorney, Agent, or Firm*—John H. Vynalek

[57] ABSTRACT

A new and distinct variety of *Maackia amurensis* tree, characterized particularly as to novelty by its straight trunk with attractive peeling coppery bark, exceptionally vigorous grwoth and its very large showy and abundant white panicles of flowers, born upright in closely clustered panicles at the ends of thick twigs.

1 Drawing Sheet

BACKGROUND OF THE DISCLOSURE

The discovery of this disclosure is an exceptional tree belonging to *Maackia amurensis*, a species of tree which is generally appreciated to have potential in landscaping for use as a border tree or for use as an appointment specimen which has attractive foliage, very attractive bark, a dense habit, a slow rate of growth, and an attractive shape. Members of the species produce flowers similar to those of the common pea, which are conspicuous due to their groupings in dense racemes and by their coloration which is in white shades which contrast with the bright green foliage. Normally, members of this species require little maintenance, pruning and training to result in a tree of attractive shape. This species also blooms in a summer season when few other of species of trees bloom, offering a splash of color to the landscape and garden. The tree of this disclosure resulted from a planned breeding program when open pollinated seeds were taken from a selected parent, *Maackia amurensis* 'Select'. This selected tree was seen to stand apart from the parent 'Select' and sibling trees within the population due to its much higher growth rate, higher level of vigor, higher level of terminal dominance, exceptional level of attractive foliage, attractive, rounded figure, resulting from well placed strong scaffold branches, and uniformly dense presentation of terminal racemes numbering one central panicle and 6 secondary panicles per stem terminal when flowering. Following selection of this tree, it has been asexually reproduced by budding in a nursery located near Upper Freehold Township, N.J. The resulting clones of this tree have remained identical to the original selection in all distinguishing characteristics as best as I can determine.

BRIEF SUMMARY OF THE INVENTION

The plant of this application was first noticed in a row of sibling seedlings. It stood out because of its straight trunk and exceptionally vigorous growth, being more than one-third taller than the other seedling grown plants in the same and adjacent rows. The tree was transplanted and grown on to blooming age. It bears very showy and abundant white panicles of flowers, born upright in closely clustered panicles at the ends of thick twigs. I have caused the plant to be asexually reproduced by bud grafting and find that it comes true in successive generations which have been produced over time.

The tree of this disclosure is more stately, forms a denser, more uniformly rounded and attractive canopy, and has a more prolific and a more conspicuously attractive flowering habit when compared with the species. Specifically, the individual flowers of this tree are slightly larger than typical flowers of the species, while their color is white, typical of the species. The flowering of this tree differs from the species in the large size and density of the flower clusters, being held upright or vertical on the ends of the twigs. The leaf color is darker than other trees of the species with the individual leaflets about twice as thick. The branch density of this tree is greater than the parent tree. The leaves are larger than the parent which has leaves 16 to 20 cm. long and 6 to 8 cm. wide. The leaflets are also larger than those of the parent tree which are 4 cm. long and 2.2 cm. wide. The nodes are wider apart than that of the parent tree which has nodes 6 cm. apart. Also the color of the bark of this tree is different from the parent which has a color of brownish orange 2.5 YR 5/9. The fall foliage color and leaf fall date do not differ from other trees of the species.

DESCRIPTION OF THE DRAWINGS

This new variety of Maackia is illustrated by the accompanying photographic drawings and depicts the plant by the best possible color representation using color photography.

BOTANICAL DESCRIPTION OF THE PLANT

Figure 2:
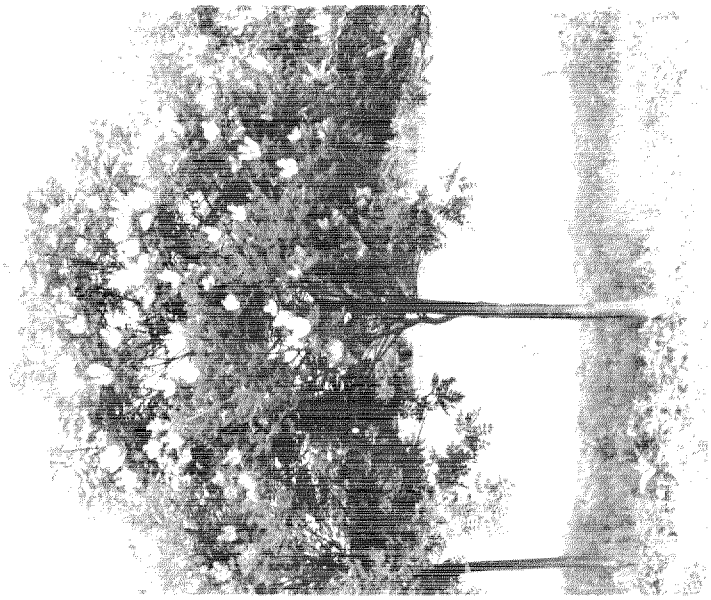
FIG. 2 is a view showing the entire tree.
Figure 1:
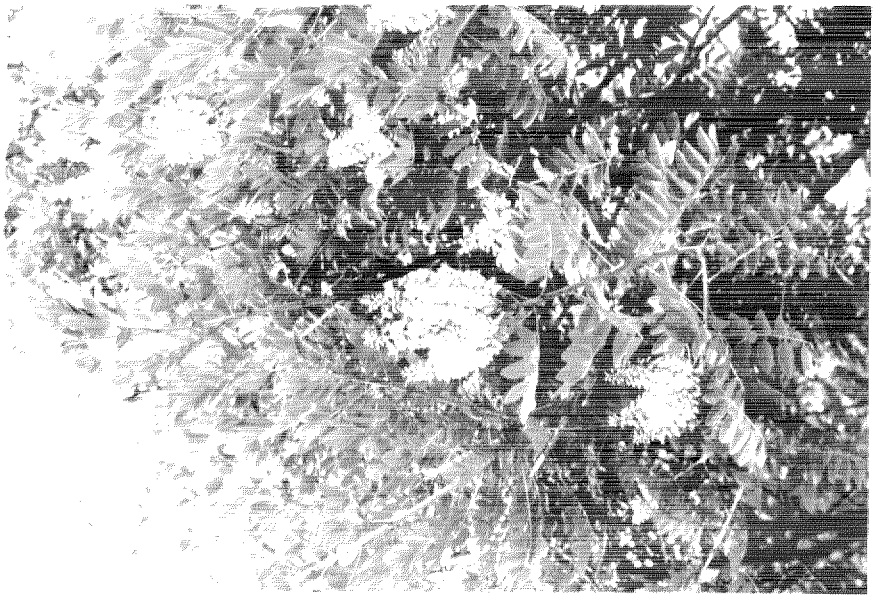
FIG. 1 is a view showing the detail of the flower panicles.

All color references below are measured against Munsell Limit Color Cascade. Colors are approximate as color depends on horticultural practices such as light level and fertilization rate, among others.

Parentage:

*Seed parent.*—*Maackia amurensis* 'Select'.

*Pollen parent.*—Unknown.

Tree: Medium height and spreading, dense crown, and very hardy.

*Trunk.*—Stocky and smooth, attractive, peeling coppery bark, color: Strong brown 2.5 YR 4/7.

*Branches.*—Stocky and smooth, densely borne at an average 60 degree angle from the perpendicular central trunk. Color — Moderate olive, 5Y 4/3. Lenticels — Small; numbering 2 to 3 per cm of twig length.

*Leaves.*—Quantity — Abundant, pinnately compound, leaflets opposite on stem. The leaf pose is upright on the twigs at about a 55 degree angle from the twig. Length — 20 to 22 cm. Width — 8 to 10 cm. Shape — Pinnately compound; 13 leaflets per stem; Leaflets 5 cm long; 2.4 cm wide. Color — Moderate olive green, 5GY 4/3. Margin — Smooth edge. Petiole — Medium. Internode length — 8 cm. Glands — None.

*Flower buds.*—Flowers borne in the summer on new growth shoots and not noticeable on winter twigs. The flowering dates of the tree are slightly later than sibling trees which are normally August 1 to August 20. Quantity — Abundant; borne in clustered racemes; one large central panicle surrounded by 6 smaller panicles. Size — Large; central panicle 14 cm long, ancillary panicles 8 to 10 cm long; 110 to 190 florets per panicle.

*Flowers.*—Size — 1.2 cm long and 0.5 cm wide. Color — White, typical of other members of species. Number of petals — 4. Shape of petals — Ovate. Size of petals — Length 0.5 cm. Width 0.3 cm. Color — White.

*Fruits.*—Linear oblong pods; not conspicuous. When borne — Fall. Abundance — Not abundant. Size — 3.5 to 4.5 cm long. Color — Strong yellowish brown; 10 YR 5/6.

I claim:

1. A new and distinct variety of *Maackia amurensis* tree, as illustrated and described, characterized particularly as to novelty by its straight trunk with attractive peeling coppery bark, exceptionally vigorous growth and its very large showy and abundant white panicles of flowers, born upright in closely clustered panicles at the ends of thick twigs.

* * * * *